United States Patent [19]

Bellani et al.

[11] Patent Number: 4,894,237

[45] Date of Patent: Jan. 16, 1990

[54] ANTIINFLAMMATORY PHARMACEUTICAL COMPOSITION ENDOWED WITH SUSTAINED EFFECT FOR TOPICAL USE

[75] Inventors: Pietro Bellani; Luigi Valcarenghi, both of Milan, Italy

[73] Assignee: Cooperativa Farmaceutica Soc. Coop. R.L., Milan, Italy

[21] Appl. No.: 234,182

[22] Filed: Aug. 22, 1988

[30] Foreign Application Priority Data

Sep. 4, 1987 [IT] Italy ................................ 21981A/87

[51] Int. Cl.⁴ ................................................ A61K 9/14
[52] U.S. Cl. ...................................... 424/486; 424/484; 424/488
[58] Field of Search .......................... 424/488, 484, 486

[56] References Cited

U.S. PATENT DOCUMENTS

| | | | |
|---|---|---|---|
| 3,637,767 | 1/1972 | Alvarex | 549/554 |
| 4,341,759 | 7/1982 | Bogentoft et al. | 424/468 |
| 4,716,041 | 12/1987 | Kjornaes et al. | 424/470 |

Primary Examiner—Thurman K. Page
Attorney, Agent, or Firm—Walter H. Schneider

[57] ABSTRACT

A pharmaceutical composition comprising as the active principle the piperazine salt of (S) 6-methoxy-α-methyl-2-naphthaleneacetic acid in highly micronized form, suited carriers in which the active principle is scarcely soluble, surfactants, preserving agents and an hydrophilic, pH-independent, matrix consisting of alkyl derivatives of cellulose and/or polyvinylalcohol. The sustained release of the antiinflammatory compositions allows the treatment of affections by means of a single daily administration of the same.

9 Claims, No Drawings

ANTIINFLAMMATORY PHARMACEUTICAL COMPOSITION ENDOWED WITH SUSTAINED EFFECT FOR TOPICAL USE

The present invention refers to a pharmaceutical composition having a prolonged antiinflammatory activity, suited for the topical administration.

More particularly, the composition of the invention comprises an antiinflammatory non steroidal compound, the piperazine salt of (S) 6-methoxy-α-methyl-2-naphthaleneactic acid or naproxen piperazine salt, suitably mixed with suited agents from which the latter is released in controlled way during several hours, so as to allow the daily dosage required for the treatment to be administered only once a day.

The pharmaceutical composition according to the invention may be suitably formulated in form of cream, emulsion or gel for topical administration. The active principle, piperazine salt of (S) 6-methoxy-α-methyl-2-naphthaleneacetic acid is contained in micronized form in the weight percentage from 5 to 20%, in admixture with suited carriers wherein the active principle is scarcely soluble, in the weight percentage from 70 to 90%, preserving agents in the weight percentage from 0.1 to 0.2, suited surfactants in the weight percentage from 0.1 to 3% and an hydrophilic matrix, independent on pH, constituted by alkyl derivatives of cellulose, preferably hydroxy ethylcellulose, and/or polivinyl alcohol in the weight percentage from 1.4 to 4%.

More preferably, the composition of the invention consists of 8–15% of the active principle, 80 to 85% of said carriers and 1.5 to 3.5% of said hydrophilic matrix.

Suitable carriers wherein the active principle is dispersed are polyethylene glycol (MW 190–420), propylene glycol, glycerine, purified water and isopropyl alcohol, particularly preferred are purified water and glycerine. Preferred preservative agents are methyl p-hydroxybenzoate and propyl-p-hydroxybenzoate and preferred surfactants are polysorbate 80, polysorbate 20 and octoxinol, more preferably polysorbate 80.

The piperazine salt of (S) 6-methoxy-α-methyl-2-naphthaleneacetic acid is micronized so that 95% of the particles has a diameter form 2 to 20μ.

The following non limitative example further illustrates the invention.

EXAMPLE

Preparation of a gel of piperazine salt of (S) 6-methoxy-α-methyl-2-naphthaleneacetic acid 35 kg of purified water were charged in an inox vessel provided with heating jacket, thermostatized at 90°–95° C.

72 g of methyl-p-hydroxybenzoate and 30 g of propyl-p-hydroxybenzoate were then added under stirring. When the solution was complete, the temperature was lowered to 50° C. and 6.0 kg of glycerol, 300 g polysorbate 80 and 7.2 kg of micronized (2–10μ) piperazine salt of (S) 6-methoxy-α-methyl-2-naphthaleneacetic acid were added.

1.02 kg of hydroxyethylcellulose were dispersed at room temperature in 10 kg of purified water and added to the dispersion of piperazine salt of (S) 6-methoxy-α-methyl-2-naphthaleneacetic acid kept under stirring up to complete homogenization and swelling. The gel mass so obtained was distributed in amounts of 50 g each and charged for confectioning in suited tubes.

We claim:

1. Sustained effect pharmaceutical composition, suited for the topical administration, comprising as the active principle the piperazine salt of (S) 6-methoxy-α-methyl-2-naphthaleneacetic acid in micronized form in admixture with primary carriers selected in the group consisting of polyethylene glycol, propylen glycol, glycerine, purified water and isopropyl alcohol or mixtures thereof and with an hydrophylic, pH-independent, matrix consisting of cellulose alkyl derivative of cellulose and/or polyvinyl alcohol.

2. A composition according to claim 1 wherein the active principle is present in the weight percentage from 5 to 20%.

3. A composition according to claim 1 wherein the active principle is present in the weight percentage from 8 to 15%.

4. A composition according to claim 1, wherein the primary carriers are present in the weight percentage from 70 to 90% and the hydrophylic matrix from 1.4 to 4%.

5. A composition according to claim 1, wherein the primary carriers are present in the weight percentage from 80 to 85% and the hydrophylic matrix from 1.5 to 3.5%.

6. A composition according to claim 1 further comprising suitable surfactant and preserving agents.

7. A composition according to claim 1 in which the piperazine salt of (S) 6-methoxy-α-methyl-2-naphthaleneacetic acid has particle size from 2 to 20μ.

8. A composition according to claim 1 in which the surfactant is selected in the group consisting of polysorbate 20, polysorbate 80 and octoxinol in the weight percentage from 0.1 to 3% and that the preserving agent is a mixture of methyl- and propyl-p-hydroxybenzoate.

9. A composition according to claim 1 in which the hydrophylic matrix consists of hydroxyethylcellulose.

* * * * *

UNITED STATES PATENT AND TRADEMARK OFFICE
CERTIFICATE OF CORRECTION

PATENT NO. : 4,894,237

DATED : January 16, 1990

INVENTOR(S) : Pietro Bellani; Luigi Valcarenghi

It is certified that error appears in the above-identified patent and that said Letters Patent is hereby corrected as shown below:

On the Title page, under "Foreign Application Priority Data", "Sep. 4, 1987" should read ---Sep. 22, 1987---.

Signed and Sealed this

Fifth Day of March, 1991

Attest:

HARRY F. MANBECK, JR.

Attesting Officer

Commissioner of Patents and Trademarks